United States Patent
Jugl et al.

(10) Patent No.: US 9,370,624 B2
(45) Date of Patent: Jun. 21, 2016

(54) ASSEMBLY FOR USE IN A DRUG DELIVERY DEVICE

(75) Inventors: Michael Jugl, Frankfurt am Main (DE); Martin Otten, Frankfurt am Main (DE)

(73) Assignee: SANOFI-AVENTIS DEUTSCHLAND GMBH, Frankfurt am Main (DE)

(*) Notice: Subject to any disclaimer, the term of this patent is extended or adjusted under 35 U.S.C. 154(b) by 960 days.

(21) Appl. No.: 13/516,062

(22) PCT Filed: Dec. 16, 2010

(86) PCT No.: PCT/EP2010/069869
§ 371 (c)(1),
(2), (4) Date: Sep. 12, 2012

(87) PCT Pub. No.: WO2011/073307
PCT Pub. Date: Jun. 23, 2011

(65) Prior Publication Data
US 2013/0018328 A1   Jan. 17, 2013

(30) Foreign Application Priority Data
Dec. 18, 2009 (EP) .................................. 09180005

(51) Int. Cl.
*A61M 5/315* (2006.01)

(52) U.S. Cl.
CPC ....... *A61M 5/31513* (2013.01); *A61M 5/31515* (2013.01); *A61M 5/31535* (2013.01); *A61M 5/31583* (2013.01)

(58) Field of Classification Search
CPC ..................... A61M 5/31515; A61M 5/31535; A61M 5/31583; A61M 5/31513
See application file for complete search history.

(56) References Cited

U.S. PATENT DOCUMENTS

| 1,718,601 A | 6/1929 | Smith |
| 4,221,218 A | 9/1980 | Pfleger |
| 2008/0287883 A1 | 11/2008 | Radmer et al. |

FOREIGN PATENT DOCUMENTS

| WO | 94/21213 | 9/1994 |
| WO | 2004/014476 | 2/2004 |
| WO | 2005/018721 | 3/2005 |
| WO | 2005/099793 | 10/2005 |
| WO | 2008/063529 | 5/2008 |
| WO | 2009/036496 | 3/2009 |

OTHER PUBLICATIONS

European Search Report for European App. No. 09180005, completed May 31, 2010.
International Search Report for Int. App. No. PCT/EP2010/069869, completed Apr. 8, 2011.

*Primary Examiner* — Bradley Osinski
(74) *Attorney, Agent, or Firm* — McDonnell Boehnen Hulbert & Berghoff LLP

(57) ABSTRACT

The present invention relates to a piston for a cartridge for a drug delivery device comprising: at least one annular sealing surface to radially abut against an inner side wall of a cartridge, a distal surface to confine a drug receiving volume of the cartridge, a thrust receiving surface adapted to receive a thrust exerting plunger of a drug delivery device for displacing the piston in a proximal direction relative to the side wall, wherein the thrust receiving surface comprises numerous centering elements protruding from the thrust receiving surface towards the plunger and wherein the centering elements comprise an outer shape and geometry that matches with a corresponding receptacle of the plunger, and wherein the centering elements are arranged and aligned on the circumference of an imaginary annular or circular structure.

15 Claims, 5 Drawing Sheets

ASSEMBLY FOR USE IN A DRUG DELIVERY DEVICE

CROSS REFERENCE TO RELATED APPLICATIONS

The present application is a U.S. National Phase Application pursuant to 35 U.S.C. §371 of International Application No. PCT/EP2010/069869 filed Dec. 16, 2010, which claims priority to European Patent Application No. 09180005.2 filed on Dec. 18, 2009. The entire disclosure contents of these applications are herewith incorporated by reference into the present application.

FIELD OF THE INVENTION

The present invention generally relates to a piston being slidably disposed in a cartridge that contains a medicinal product to be dispensed by means of a drug delivery device, such as a pen-type injector. Moreover, the invention relates to a thrust-transferring interface between a cartridge's piston and a plunger of the drug delivery device being adapted to exert thrust to said piston.

BACKGROUND

User operated drug delivery devices are as such known in the prior art. They are typically applicable in circumstances, in which persons without formal medical training, i.e., patients, need to administer an accurate and predefined dose of a medicinal product, such as heparin or insulin. In particular, such devices have application, where a medicinal product is administered on a regular or irregular basis over a short term or long-term period.

In order to accommodate with these demands, such devices have to fulfil a number of requirements. First of all, the device must be robust in construction, yet easy to use in terms of handling and in understanding by the user of its operation and the delivery of the required dose or medicament. The dose setting must be easy and unambiguous. Where the device is to be disposable rather than reusable, the device should be inexpensive to manufacture and easy to dispose. Moreover, the device should be suitable for recycling. To meet these requirements, the number of parts required to assemble the device and the number of material types the device is made from need to be kept to a minimum.

Such pen-typed injectors are typically adapted to receive a replaceable and/or disposable cartridge containing the medicinal product to be dispensed by means of the device. The cartridge comprises an outlet to be coupled with a piercing element, e.g. an injection needle, a cannula or the like in a fluid transferring way. Further and in order to expel a predefined dose of the medicinal product, a plunger of a drug delivery device is adapted to act on the piston for displacing said piston by a predefined distance in distal, thus dose-dispensing direction.

FIG. 1 shows a cross-sectional illustration of a piston 16 slidably disposed inside a circumferential cylindrical wall 24 of a cartridge 23. The cartridge 23 is arranged inside a drug delivery device that comprises a proximal housing component 20 and a cartridge holder 22. The housing 20 accommodates a not further illustrated drive mechanism, that serves to drive a piston rod 10 and a bearing disc 12 in a distal axial direction, hence downward in the illustration of FIG. 1. For this purpose, the bearing disc 12 is rotatably mounted on a lower, hence distally located end section of the piston rod 10.

The radial dimensions of the bearing disc 12 substantially match with the size of the proximal end face of the piston 16.

The piston 16 comprises two annular sealing surfaces 25 radially abutting against the inner side wall 24 of the cartridge 23. In this way, the piston 16 provides a durable and leak-proof seal for the medicinal product contained in the cartridge 23. As can be seen in the cross-section of FIG. 1 and as further illustrated in a top view illustration of FIG. 2, the thrust receiving surface comprises four rectangularly shaped distance elements, which in the course of a mass production process are adapted to prevent mutual adhering of pistons, e.g. in a feeding arrangement.

In the illustration of FIG. 1, the bearing disc 12 and the proximal end face, the thrust receiving surface of the piston 16, are not yet in mutual contact. During dose dispensing, the piston rod 10 typically becomes subject to a rotative movement. Due to a threaded engagement with a radially inwardly protruding thread 18, the piston rod 10 is displaced in distal direction when rotated. Consequently, the bearing disc 12 gets in direct contact with the proximally located thrust receiving surface of the piston 16 and in response to a further applied thrust, the piston 16 becomes displaced in distal direction, that is downwards in FIG. 1.

In practice, due to manufacturing and assembly tolerances radial position of the piston rod 10 and/or the bearing disc 12 may vary within certain limits. Hence, a piston rod 10 and/or a bearing disc 12 can be radially displaced with respect to the center of the piston 16. If not properly aligned, it may occur, that the force provided by the piston rod 10 and the bearing disc 12 is non-centrically transferred to the piston 16. Such radial offset may in turn lead to a cant or tilt of the piston 16, which is flexibly deformable to a certain extent. As a consequence, a displacement force required for distally displacing the piston 16 may substantially rise. Additionally, also the dosing accuracy may decrease when a distally directed driving force is non-centrally transferred to the piston 16.

Also, since the distance elements 14 protrude from the proximal end face of the piston 16, thrust being applied to the piston 16 is entirely received by the distance elements 14, which, as a consequence may become squeezed. However, such point stresses and squeezing effects may further have a negative impact on the dosing accuracy of the drug delivery device and its drive mechanism.

SUMMARY

It is therefore an object of the present invention to provide an improved piston for a cartridge as well as an improved plunger of a drug delivery device interacting with such pistons. In particular, the invention focuses on the plunger-piston interface of cartridges and drive mechanisms of drug delivery devices, preferably of pen-injector type. It is a further aim of the present invention to prevent non-centrally directed force transmission towards a cartridge's piston. As a further object, the invention aims to provide an improved dosing accuracy.

The present invention provides a piston for a cartridge for a drug delivery device, wherein the piston comprises at least one annular sealing surface to radially abut against an inner side wall of a cartridge, being typically of cylindrical shape. The piston is adapted to be slidably disposed in the cartridge and to provide a durable and leak-proof seal. The cartridge itself is typically designed as carpule or vial, in which the piston is slidably disposed for the purpose of expelling a liquid content of the cartridge via an outlet located at an opposite, hence, distal end portion of the cartridge.

The piston further comprises a thrust receiving surface, which is adapted to receive a thrust exerting plunger of a drug delivery device. When in abutment position, the plunger serves to displace the piston in a distal direction relative to the side wall of the cartridge, thus expelling a pre-defined dose of the medicinal fluid. Opposite its thrust receiving surface, the piston comprises a distal surface adapted to confine a drug receiving volume of the cartridge.

The thrust receiving surface, which in an assembly configuration of the cartridge inside a drug delivery device faces towards a plunger, comprises numerous centering elements protruding from the thrust receiving surface towards the plunger. Said centering elements further comprise an outer shape and geometry that substantially matches with a corresponding receptacle of the plunger. Typically, axial and lateral shape of the centering elements and the corresponding receptacle match in such a way, that the centering elements can be almost entirely inserted into the receptacle. In other words, the receptacle of the plunger comprises such a shape and geometry, that the centering elements protruding from the thrust receiving surface of the piston can be entirely received therein, thereby providing mutual lateral alignment of piston and plunger.

Preferably, the radial position and orientation of the centering elements on the thrust receiving surface of the piston corresponds to the radial position and orientation of the receptacle on the plunger, provided that plunger and piston are mutually centered. In this way, any manufacturing or assembly tolerances can be inherently compensated upon insertion of the centering element into its corresponding receptacle in the plunger. In case that after assembly of the drug delivery device piston and plunger are positioned at a certain radial offset, by moving the plunger in distal direction, the plunger and/or the cartridge preferably become subject to a radially directed centering movement when the centering elements match with the corresponding receptacle of the plunger.

The centering elements are arranged and aligned on the circumference of an imaginary annular or circular structure in the plane of the thrust receiving surface.

The circular structure may be circular-symmetric but may also be oval or elliptical. By making use of such a circular arrangement, mutual centering and alignment of piston and plunger can be easily attained when the circular structure is inherently symmetric to the centre of the thrust receiving surface.

In a preferred embodiment, the centering elements and/or the circular structure corresponds with a circular shape of the receptacle of the plunger. In this way, not only the structure and shape of numerous centering elements but also their mutual distance and alignment matches with the receptacle of the plunger.

In this embodiment, the at least one centering element may also comprise a rectangular and/or arcuate shape in a plane parallel to the thrust receiving surface. Further, it is of particular benefit, when various centering elements are arranged at a distance with respect to each other on the circumference of said imaginary circular or annular structure.

Each of the centering elements may for instance comprise a somewhat rectangular shape, wherein each centering element is slightly bended according to the radius and circumference of the imaginary circular structure.

By having a circular shaped receptacle or groove on the plunger and by having numerous centering elements distributed along the circumference of the imaginary circle, a mutual radial centering of piston and plunger as well as a mutual orientation in the transverse plane can be achieved irrespective on the orientation of the piston and its centering elements in the plane of the thrust receiving surface.

Furthermore, and according to another preferred aspect, the centering elements comprise an arcuate shape in a plane parallel to the thrust receiving surface. Hence, the shape of at least some, preferably of all centering elements matches with the shape and geometry of the ring-like or annular receptacle of the plunger. This way, when plunger and piston are arranged with a slight lateral offset, almost all available centering elements contribute in a rather similar way to a mutual alignment and centering of piston and plunger.

According to another preferred embodiment of the invention, the at least one centering element is integrally formed with a body of the piston. Typically, the piston is manufactured by injection moulding. It may comprise thermoplastic materials and/or natural or synthetic rubber. At least one of the centering elements may further act as a spacer or distance element that serves to prevent mutual adhering of pistons in the course of a mass production process. Said at least one particular centering element comprises a knob-like shape.

In a further preferred embodiment, at least one centering element is tapered in direction towards the plunger. Accordingly, also the receptacle provided in the plunger comprises a corresponding tapered cross-section, which allows to entirely receive the centering element therein.

In a further preferred embodiment, the at least one centering element comprises a bevelled lateral surface. Since the receptacle is correspondingly shaped, by way of such bevelled surfaces, a radial adjustment of piston and plunger can be attained when mutually corresponding bevelled surfaces of receptacle and centering element get in contact in the course of an axially and distally directed displacement of the plunger.

Preferably, the bevelled lateral surface of the at least one centering element is oriented at an angle of 20° to 80° with respect to the plane of the thrust receiving surface. More preferably, the bevelled lateral surface of the centering element is oriented at an angle between 30° to 60°, most preferably, the angle is around 45°.

Furthermore, it is beneficial, when at least one centering element is substantially triangular or convex in shape in a plane perpendicular to the thrust receiving surface. Hence, the bevelled lateral surface does not necessarily have to be rectilinear. It can be bended, such as to facilitate mutual radial alignment of piston and plunger in the course of a distally directed movement of the plunger.

According to another preferred embodiment of the invention, the ratio of at least one centering element's axial extension, that is the extension substantially perpendicular to the thrust receiving surface, versus its radial expansion, that is the expansion parallel to the plane of the thrust receiving surface, is larger or equal than 0.6. Such a ratio is particularly beneficial for the purpose of radially centering plunger and piston or cartridge in the course of a distally directed movement of the plunger towards the piston.

In another independent aspect, the invention further relates to a plunger of a drive mechanism of a drug delivery device, such as a pen-type injector. The plunger comprises an end face adapted to but against a thrust receiving surface of a piston being slidably disposed in a drug containing cartridge. The end face of the plunger facing towards the piston comprises at least one receptacle being adapted to receive a centering element that protrudes from the thrust receiving surface of the piston.

The receptacle of the sface as well as the centering element protruding from the piston's thrust receiving surface mutually match in size, shape and geometry. Also, the receptacle comprises a somewhat circular or annular shape that corresponds with the position and/or alignment of the centering element provided on the thrust receiving surface. In this way, an eventual radial offset in position or orientation of plunger and/or piston or cartridge can be compensated in the course of bringing plunger and piston in a mutual abutment configuration.

When shape and geometry of the receptacle matches with the shape and geometry and/or alignment of the piston's centering element, the end face of the plunger may almost entirely but against the thrust receiving surface of the piston. In this way, thrust provided by the plunger can be evenly distributed across the plunger-piston-interface. Also, point stresses as they are arising in the prior art and their negative impact on dosing accuracy can be effectively reduced.

In preferable embodiments, the receptacle disposed on the end face of the plunger comprises a substantially U- or V-shaped groove of circular geometry in the plane of the end face. By having a circular symmetric receptacle, a plurality of centering elements spaced apart from each other and being arranged on an imaginary circumference of a corresponding circle can be inserted into said receptacle, irrespective of the orientation of the piston in the plane of its thrust receiving surface.

According to still another preferred embodiment, the plunger comprises an axially displaceable piston rod and a radially extending bearing disc. The bearing disc is rotatably supported at a distal end portion of the piston rod. Preferably, the bearing disc comprises the receptacle at its end face pointing towards the piston, when the drug delivery device is finally assembled.

In a further independent aspect the invention also refers to a cartridge for a drug delivery device that comprises a substantially cylindrical cartridge body providing a drug receiving volume at least partially filled with a medicament and being sealed by means of a piston as described above. The medicament is typically intended for injection into biological tissue of a patient.

Moreover, the invention also refers to a drug delivery device for dispensing a pre-defined amount of a liquid drug and being further adapted to receive a cartridge having a piston as described above. The drug delivery device further comprises a drive mechanism having a plunger comprising at least one receptacle being adapted to receive a centering element protruding from a thrust receiving surface of the piston of said cartridge.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(w-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36[Asp28] Exendin-4(1-39),
des Pro36[IsoAsp28] Exendin-4(1-39),
des Pro36[Met(O)14, Asp28] Exendin-4(1-39),
des Pro36[Met(O)14, IsoAsp28] Exendin-4(1-39),
des Pro36[Trp(O2)25, Asp28] Exendin-4(1-39),
des Pro36[Trp(O2)25, IsoAsp28] Exendin-4(1-39),
des Pro36[Met(O)14 Trp(O2)25, Asp28] Exendin-4(1-39),
des Pro36[Met(O)14 Trp(O2)25, IsoAsp28] Exendin-4(1-39); or
des Pro36[Asp28] Exendin-4(1-39),
des Pro36[IsoAsp28] Exendin-4(1-39),
des Pro36[Met(O)14, Asp28] Exendin-4(1-39),
des Pro36[Met(O)14, IsoAsp28] Exendin-4(1-39),
des Pro36[Trp(O2)25, Asp28] Exendin-4(1-39),
des Pro36[Trp(O2)25, IsoAsp28] Exendin-4(1-39),
des Pro36[Met(O)14 Trp(O2)25, Asp28] Exendin-4(1-39),
des Pro36[Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36[Asp28] Exendin-4(1-39)-Lys6-NH2,
des Asp28 Pro36, Pro37, Pro38Exendin-4(1-39)-NH2,
H-(Lys)6-des Pro36, Pro38[Asp28] Exendin-4(1-39)-NH2,
H-Asn-(Glu)5des Pro36, Pro37, Pro38[Asp28] Exendin-4(1-39)-NH2,
des Pro36, Pro37, Pro38[Asp28] Exendin-4(1-39)-(Lys)6-NH2,
H-(Lys)6-des Pro36, Pro37, Pro38[Asp28] Exendin-4(1-39)-(Lys)6-NH2,
H-Asn-(Glu)5-des Pro36, Pro37, Pro38[Asp28] Exendin-4 (1-39)-(Lys)6-NH2,
H-(Lys)6-des Pro36[Trp(O2)25, Asp28] Exendin-4(1-39)-Lys6-NH2, H-des Asp28 Pro36, Pro37, Pro38[Trp(O2)25] Exendin-4(1-39)-NH2,
H-(Lys)6-des Pro36, Pro37, Pro38[Trp(O2)25, Asp28] Exendin-4(1-39)-NH2,
H-Asn-(Glu)5-des Pro36, Pro37, Pro38[Trp(O2)25, Asp28] Exendin-4(1-39)-NH2,
des Pro36, Pro37, Pro38[Trp(O2)25, Asp28] Exendin-4(1-39)-(Lys)6-NH2,
H-(Lys)6-des Pro36, Pro37, Pro38[Trp(O2)25, Asp28] Exendin-4(1-39)-(Lys)6-NH2,
H-Asn-(Glu)5-des Pro36, Pro37, Pro38[Trp(O2)25, Asp28] Exendin-4(1-39)-(Lys)6-NH2,
H-(Lys)6-des Pro36[Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38[Met(O)14, Asp28] Exendin-4(1-39)-NH2,
H-Asn-(Glu)5-des Pro36, Pro37, Pro38[Met(O)14, Asp28] Exendin-4(1-39)-NH2,
des Pro36, Pro37, Pro38[Met(O)14, Asp28] Exendin-4(1-39)-(Lys)6-NH2,
H-(Lys)6-des Pro36, Pro37, Pro38[Met(O)14, Asp28] Exendin-4(1-39)-(Lys)6-NH2,
H-Asn-(Glu)5 des Pro36, Pro37, Pro38[Met(O)14, Asp28] Exendin-4(1-39)-(Lys)6-NH2,
H-Lys6-des Pro36[Met(O)14, Trp(O2)25, Asp28] Exendin-4(1-39)-Lys6-NH2,
H-des Asp28 Pro36, Pro37, Pro38[Met(O)14, Trp(O2)25] Exendin-4(1-39)-NH2,
H-(Lys)6-des Pro36, Pro37, Pro38[Met(O)14, Asp28] Exendin-4(1-39)-NH2,
H-Asn-(Glu)5-des Pro36, Pro37, Pro38[Met(O)14, Trp(O2)25, Asp28] Exendin-4(1-39)-NH2,
des Pro36, Pro37, Pro38[Met(O)14, Trp(O2)25, Asp28] Exendin-4(1-39)-(Lys)6-NH2,
H-(Lys)6-des Pro36, Pro37, Pro38[Met(O)14, Trp(O2)25, Asp28] Exendin-4(S1-39)-(Lys)6-NH2,
H-Asn-(Glu)5-des Pro36, Pro37, Pro38[Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be apparent to those skilled in the art that various modifications and variations can be made to the present invention without departing from its spirit and scope. Further, it is to be noted, that any reference signs used in the appended claims are not to be construed as limiting the scope of the present invention.

BRIEF DESCRIPTION OF THE DRAWINGS

Without limitation, the present invention will be explained in greater detail below in connection with preferred embodiments and with reference to the drawings in which.

DETAILED DESCRIPTION

Figure 1:
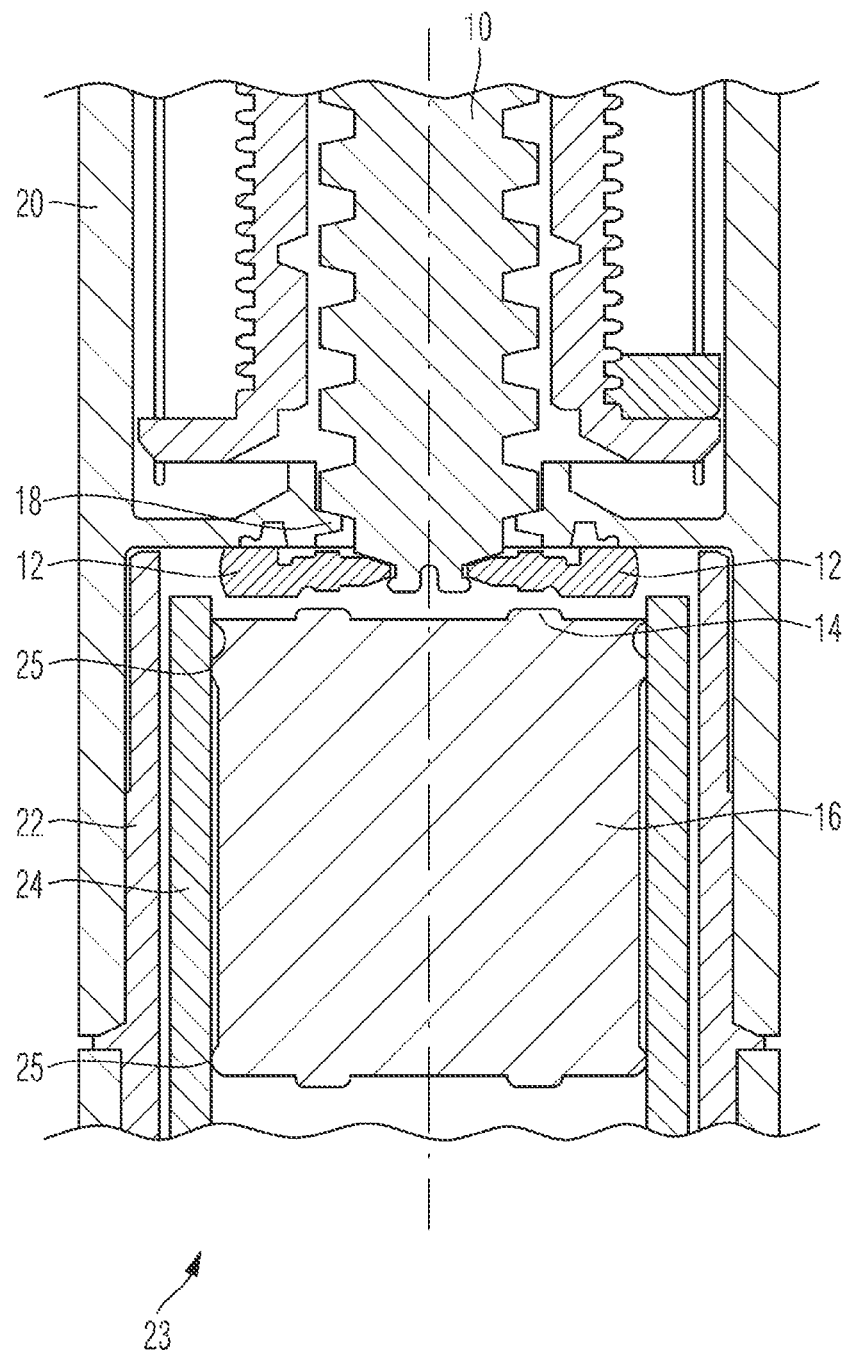
FIG. 1 illustrates a cross-section of a plunger-piston-interface region inside a pen-type injector according to the prior art.
Figure 2:
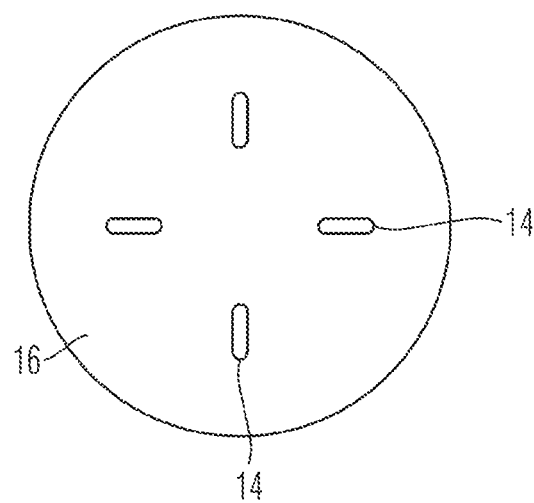
FIG. 2 illustrates a top view of the piston according to FIG. 1.
Figure 3:
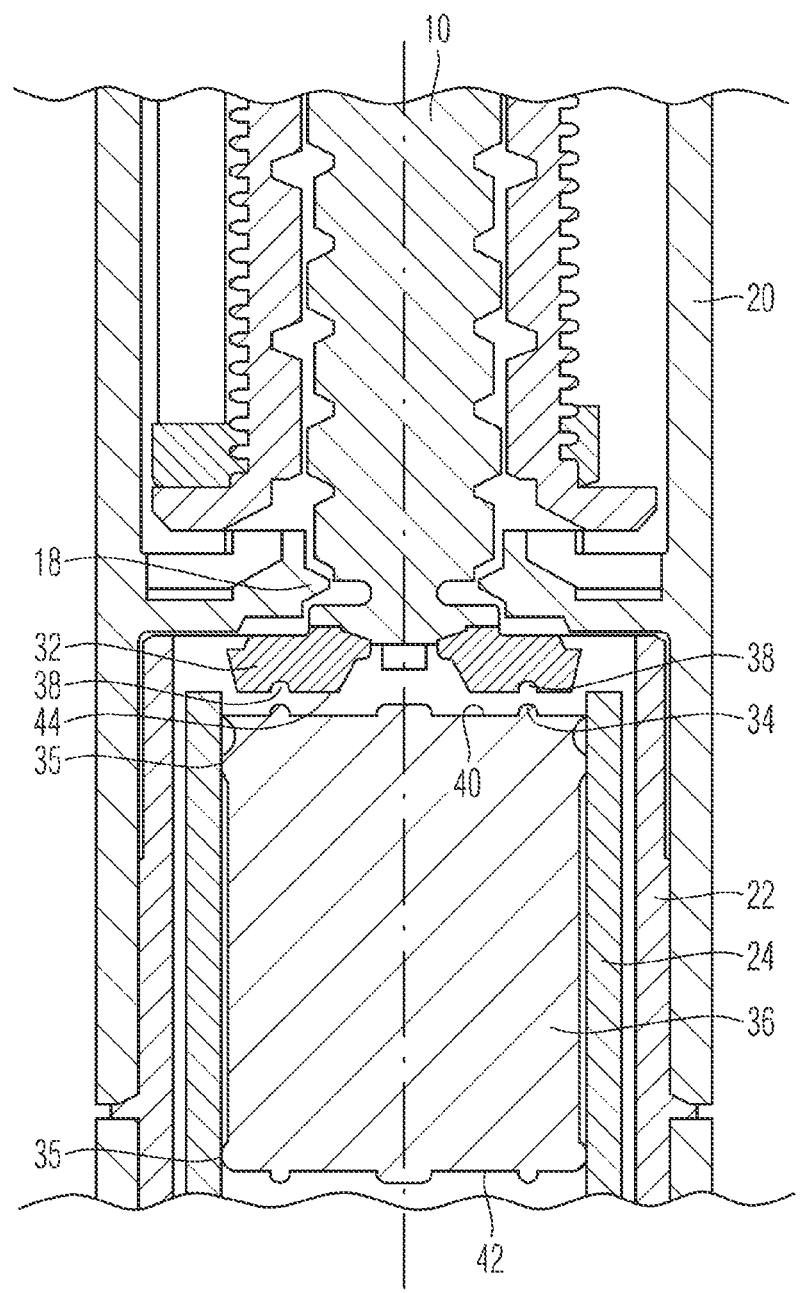
FIG. 3 shows a cross section of a plunger-piston-interface region according to the present invention, FIG. 4 in a perspective illustration shows a piston according to the present invention.

The enlarged illustration of FIG. 3 shows a drug delivery device in cross-section in a middle section, where a plunger buts against a proximal end face 40 of a piston 36. The drug delivery device as illustrated comprises a housing 20 and a cartridge holder 22. The cartridge holder 22 is adapted to receive a cartridge 33 having a substantially cylindrical side wall 24. Inside the cartridge 33, a piston 36 is slidably disposed. The piston 36 comprises two sealing surfaces 35 radially abutting against the inner side wall 24 of the cartridge 33. In this way, the piston 36 provides a durable and leak-proof seal for a drug receiving volume of the cartridge 33, which is confined in proximal direction by the lower, hence distal end face 42 of the piston 36.

Figure 4:
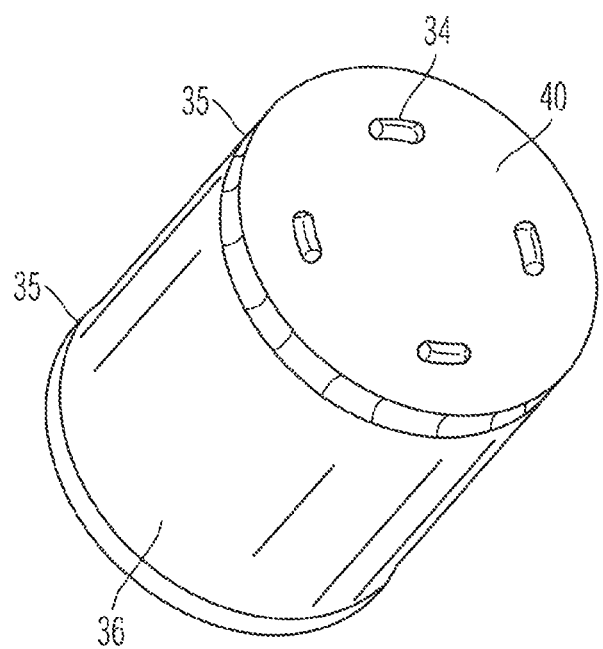

Opposite its distal surface 42, the piston 36 comprises numerous centering elements 34, which according to the illustration of FIG. 4 are of substantially rectangular shape. The centering elements 34 are integrally formed with the body 36 of the piston, e.g. by way of injection moulding. The centering elements 34 are also arranged on the circumference of an imaginary circle. Accordingly, the centering element 34 are slightly bended, so as to follow the circumference of the imaginary circle. The center point of the imaginary circle typically ideally matches and overlaps with the center point of the piston 36 itself.

As further illustrated in the cross-section of FIG. 3, the plunger of the drug delivery device comprises a piston rod 10 threadedly engaged with a thread 18 being integrally formed with the housing 20. At the lower, distal end of the piston rod 10 there is rotatably mounted a bearing disc 32. At its distal surface, the bearing disc 32 comprises a circumferential groove 38, which is adapted to entirely receive the knob-like centering elements 34 protruding from the thrust receiving surface 40 of the piston 36.

In the illustrations of FIGS. 3 and 4, the groove 38 is somewhat U-shaped and the corresponding centering elements 34 of the piston 36 feature a convex shape in a plane perpendicular to the thrust receiving surface 40. Since shape and geometry of centering elements 34 matches with the shape and geometry of the receptacle 38, a mutual radial alignment of piston 36 and cartridge 33 with respect to the plunger 10, 32 can be achieved as soon as the piston rod 10 is brought into contact with the piston 36.

Since the receptacle 38 provided in the end face 44 of the bearing disc 32 is of circular symmetric shape, a mutual radial centering and alignment of piston 36 or cartridge 33 and/or bearing disc 32 and piston rod 10 can be achieved irrespective of the rotational orientation of the cartridge 33 or its piston 36.

Figure 5:
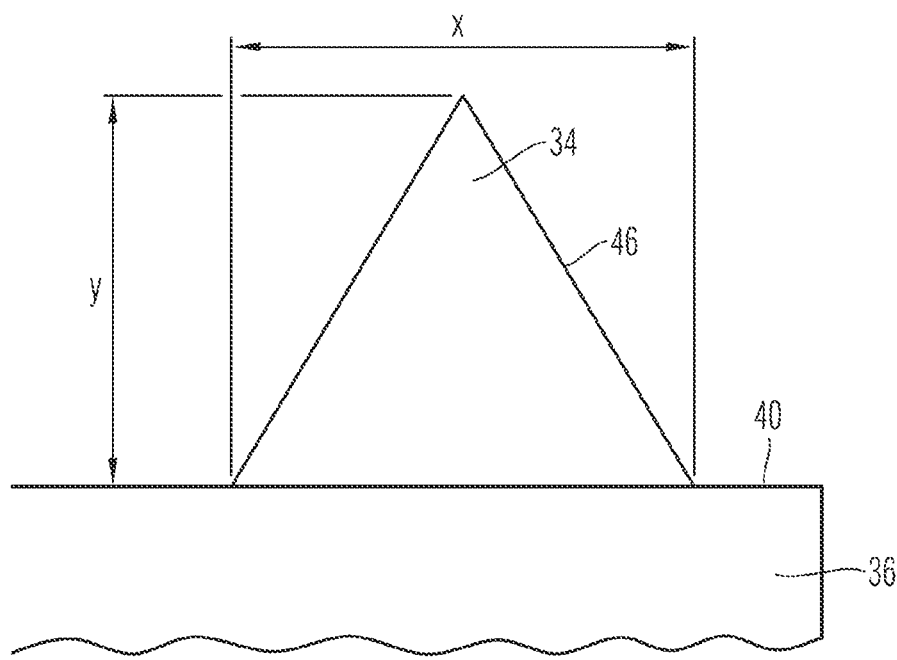
FIG. 5 shows a triangular-shaped centering element in cross-section.

In FIG. 5, a centering element 34 is separately illustrated in cross-section. Here, the centering element 34 is of substantially triangular shape. It comprises a radial extension x and an axial extension y. In preferred embodiments, the ratio of axial dimensions y to radial dimensions x of the centering element 34 is larger or equal than 0.6. Additionally, as illustrated in FIG. 5, the triangular shaped centering element 34 comprises two bevelled lateral surfaces 46.

Figure 6:
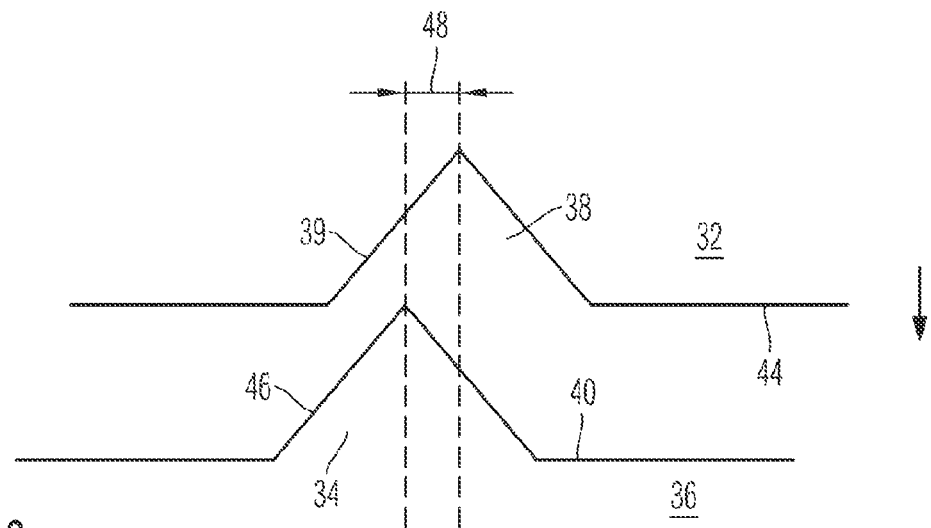
FIG. 6 shows a configuration of centering elements with respect to corresponding grooves in a bearing disc prior to mutual abutment.
Figure 7:
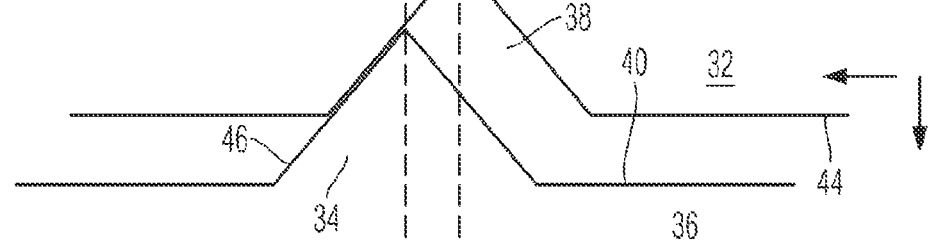
FIG. 7 is illustrative of the interface according to FIG. 6, wherein the bearing disc is radially offset but in contact with the centering element
Figure 8:
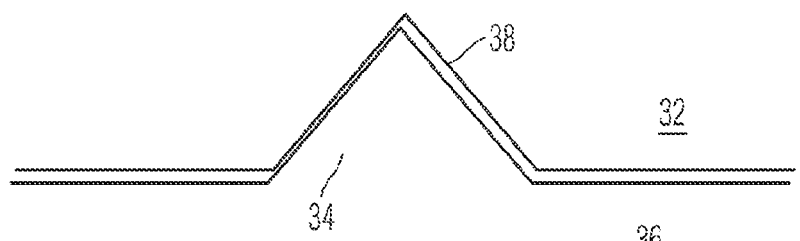
FIG. 8 shows the interface according to FIGS. 6 and 7 when a final abutment position has been reached.

Since size, shape and geometry of centering elements 34 and corresponding receptacle 38 have to match, in this case also the receptacle 38 of the bearing disc 32 comprises a V-shaped contour as illustrated in FIGS. 6 through 8.

As shown in the course of FIGS. 6 through 8, the centering element 34 and its corresponding receptacle 38 formed in the bearing disc 32 are slightly offset in radial direction by a distance 48. When the piston rod 10 is further displaced in distal direction, hence towards the piston 36, mutually corresponding bevelled surfaces 46, 39 of centering element 34 and receptacle 38 get in contact as depicted in FIG. 7. A further movement of the bearing disc 32 in distal direction, hence downward in FIG. 7, then automatically leads to a mutual radial centering of bearing disc 32 and piston 36. As indicated by the arrow pointing to the left in FIG. 7, the bearing disc 32 and/or its interconnected piston rod 10 become subject to a movement to the left.

Finally, when an end configuration has almost been reached, as illustrated in FIG. 8 has been reached, piston 36 and bearing disc 32 are almost perfectly aligned in radial direction with respect to each other. Since the depth of the receptacle 38 corresponds to the axial protrusion of the centering element 34, the distal end face 44 of the bearing disc 32 directly abuts against the thrust receiving surface 40 of the piston 36 across a comparatively large surface area. Hence, when a mutual centered configuration as illustrated in FIG. 8 has been reached, thrust exerted by the piston 10 can be evenly and homogeneously transferred to the piston 36 almost across the entire thrust receiving surface 40.

In this way point stresses can be reduced and the piston 36 is less prone to inadvertent tilt or cant during dose dispensing. This way, the driving force required to shift the piston 36 in distal direction can be kept in a comparatively moderate range.

The invention claimed is:

1. A piston and plunger combination for use in a drug delivery device comprising,
    a) a piston having a body comprising a distal end face and a proximal thrust receiving surface, wherein the piston further comprises a radial sealing surface that is configured to engage an inner sidewall of a cartridge to provide a leak proof seal;
    b) a plurality of centering elements protruding proximally from the proximal thrust receiving surface,
    c) a plunger having a distal facing end face; and
    d) a receptacle on the distal facing end face having a geometric shape and depth, where the geometric shape of the receptacle is a substantially U- or V-shaped groove of circular geometry as viewed in a plane parallel to the distal facing end face,
    wherein the plurality of centering elements are arranged on the proximal thrust receiving surface in a pattern that matches the geometric shape of the receptacle and protrude outwardly from the proximal thrust receiving surface a distance less than or equal to the depth of the receptacle such that the distal facing end face is in contact with the proximal thrust receiving surface when the plunger and piston abut,
    wherein each of the plurality of centering elements when as viewed in a plane parallel to the proximal thrust receiving surface comprise an arcuate shape.

2. The piston and plunger combination of claim 1 where the geometric shape and depth of the receptacle is configured such that the plurality of centering elements are completely received in the receptacle when the piston and plunger abut.

3. The piston and plunger combination of claim 1 where the geometric shape and depth of the receptacle are configured such that if the piston and plunger are radially offset from one another then the plunger or the piston are subjected to a radially directed centering movement when the plurality of centering elements match with the receptacle of the plunger to laterally align the piston and plunger.

4. The piston and plunger combination of claim 1 where the pattern of the plurality of centering elements and the shape of the receptacle is circular.

5. The piston and plunger combination of claim 1 where the pattern of the plurality of centering elements and the shape of the receptacle is semicircular.

6. The piston and plunger combination of claim 1 where at least one centering element is a spacer configured to prevent mutual adhering of like pistons when the pistons are mass produced.

7. The piston and plunger combination of claim 1 where at least one centering element is a knob-like protrusion.

8. The piston and plunger combination of claim 1 where the receptacle has a radius of curvature and the plurality of centering elements comprise bent rectangles that match the radius of curvature of the receptacle.

9. The piston and plunger combination of claim 1 where at least one centering element is tapered in a direction towards the plunger.

10. The piston and plunger combination of claim 1 where the plurality of centering elements are integrally formed with the body of the piston.

11. The piston and plunger combination of claim 1 where the plunger comprises an axially displaceable piston rod and a radially extending bearing disc.

12. The piston and plunger combination of claim 11 where the bearing disc is rotatably supported at a distal end portion of the piston rod and has a distal end face comprising the receptacle.

13. A drug delivery device comprising,
    a) a piston having a body comprising a distal end face and a proximal thrust receiving surface, wherein the piston further comprises a radial sealing surface that is configured to engage an inner sidewall of a cartridge to provide a leak proof seal;
b) a plurality of centering elements protruding proximally from the proximal thrust receiving surface,
c) a plunger having a distal facing end face; and
d) a receptacle on the distal facing end face having a geometric shape and depth, where the geometric shape of the receptacle is a substantially U- or V-shaped groove of circular geometry as viewed in a plane parallel to the distal facing end face,
wherein the plurality of centering elements are arranged on the proximal thrust receiving surface in a pattern that matches the geometric shape of the receptacle and protrude outwardly from the proximal thrust receiving surface a distance less than or equal to the depth of the receptacle such that the distal facing end face is in contact with the proximal thrust receiving surface when the plunger and piston abut, and
wherein each of the plurality of centering elements when as viewed in a plane parallel to the proximal thrust receiving surface comprise arcuate shape.

14. A method of correcting a radial offset between a piston and a plunger both contained in an assembled drug delivery device comprising,
a) providing a piston contained in a cartridge having a distal end face and a proximal thrust receiving surface, where the piston has a plurality of centering elements protruding proximally from the thrust receiving surface that when as viewed in a plane parallel to the proximal thrust receiving surface comprise arcuate shape, and wherein the piston further comprises a radial sealing surface that is configured to engage an inner sidewall of a cartridge to provide a leak proof seal;
b) providing a plunger within a housing of the drug delivery device, the plunger having a distal facing end face comprising a receptacle on the distal facing end face having a geometric shape and depth, where the geometric shape of the receptacle is a substantially U- or V-shaped groove of circular geometry as viewed in a plane parallel to the distal facing end face, where the plurality of centering elements are arranged on the thrust receiving surface in a pattern that matches the geometric shape of the receptacle, where the plurality of centering elements protrude outwardly from the thrust receiving surface at a depth less than or equal to the depth of receptacle such that the distal facing end face is in contact with the proximal thrust receiving surface when the plunger and piston abut; and
c) abutting the piston and the plunger to engage the plurality of centering elements with the receptacle such that a radial offset in position or orientation between the plunger and piston is corrected causing the distal facing end face of the plunger to directly contact and abut against the thrust receiving surface of the piston.

15. The method of claim 14 where the engaging of the centering elements with the receptacle further comprises contacting at least one beveled lateral surface of a centering element with a correspondingly lateral surface of receptacle to cause radial alignment of the piston and the plunger.

* * * * *